United States Patent [19]
Pennetreau et al.

[11] Patent Number: 5,382,721
[45] Date of Patent: Jan. 17, 1995

[54] PROCESS FOR THE PREPARATION OF 1,1,1,2-TETRAFLUOROETHANE

[75] Inventors: Pascal Pennetreau, Rixensart; Francine Janssens, Vilvoorde, both of Belgium; Max Braun, Burgwedel, Germany; Johannes Eicher, Garbsen, Germany; Werner Rudolph, Hanover, Germany; Eckhard Hausmann, Garbsen, Germany

[73] Assignee: Solvay (Société Anonyme), Brussels, Belgium

[21] Appl. No.: 72,759

[22] Filed: Jun. 7, 1993

[30] Foreign Application Priority Data

Jun. 9, 1992 [BE] Belgium .............. 09200533

[51] Int. Cl.⁶ ............... C07C 17/08; C07C 19/08
[52] U.S. Cl. .................... 570/166; 570/168; 570/169
[58] Field of Search ............ 570/164, 166, 167, 169, 570/168

[56] References Cited

U.S. PATENT DOCUMENTS 4,258,225  3/1981  Feiring .
5,171,900  12/1992  Eicher et al. .

FOREIGN PATENT DOCUMENTS 1196345  11/1985  Canada .
0036123  9/1981  European Pat. Off. .
0187643  7/1986  European Pat. Off. ............ 510/164
0300724  1/1989  European Pat. Off. .
0451746  10/1991  European Pat. Off. .
0462645  12/1991  European Pat. Off. .
8912614  12/1989  .
9118853  12/1991  WIPO .

*Primary Examiner*—Alan Siegel
*Attorney, Agent, or Firm*—Spencer, Frank & Schneider

[57] ABSTRACT

Process for the preparation of 1,1,1,2-tetrafluoroethane by reaction of hydrogen fluoride with a trihaloethylene according to which trifluoroethylene is chosen as trihaloethylene and the reaction is carried out in the liquid phase.

11 Claims, No Drawings

PROCESS FOR THE PREPARATION OF 1,1,1,2-TETRAFLUOROETHANE

FIELD OF THE INVENTION

The invention relates to a process for the preparation of 1,1,1,2-tetrafluoroethane (HFA-134a) by reaction of hydrogen fluoride with a trihaloethylene.

TECHNOLOGY REVIEW 1,1,1,2-Tetrafluoroethane is a synthetic compound containing carbon, fluorine and hydrogen atoms but no chlorine atoms. As such, it may constitute a substitute for fully halogenated chlorofluorinated hydrocarbons (CFC) suspected of having a harmful effect on the ozone layer. In particular, it proves to be particularly advantageous, alone or in a mixture, in certain refrigeration and air conditioning applications.

U.S. Pat. No. 4,258,225 of Du Pont discloses a process for the preparation of chlorofluoroalkanes by reaction of hydrogen fluoride with a chlorinated olefin in the liquid phase or in the gas phase, in the presence of tantalum or niobium pentafluoride. According to this document, the reaction would not take place, under the conditions adopted, in the absence of catalyst.

Patent Application WO 89/12614 of Du Pont discloses an analogous procedure using tantalum pentachloride or pentabromide as catalyst.

Patent Application WO 91/18853 of Du Pont discloses a process for the preparation of fluorinated alkanes by reaction of hydrogen fluoride with a halogenated alkane or alkene comprising at least one chlorine or bromine atom, in the presence of a dehydrating agent and of a catalyst chosen from niobium and tantalum oxides.

In order to obtain 1,1,1,2-tetrafluoroethane by hydrofluorination of olefins in the liquid phase, it is suggested in the Patent EP 300724 of ICI to use, as starting olefin, a trihaloethylene in which at least one of the halogen atoms is not fluorine.

SUMMARY OF THE INVENTION

The aim of the present invention is to provide a reliable process, which is of reduced cost and easy to carry out, for the preparation of 1,1,1,2-tetrafluoroethane by reaction of hydrogen fluoride with a trihaloethylene while presenting a high degree of conversion of the trihaloethylene and a high selectivity towards 1,1,1,2-tetrafluoroethane.

DETAILED DESCRIPTION OF THE INVENTION

The invention consequently relates to a process for the preparation of 1,1,1,2-tetrafluoroethane by reaction of hydrogen fluoride with a trihaloethylene, according to which trifluoroethylene is chosen as the trihaloethylene and the reaction is carried out in the liquid phase.

The reaction of hydrogen fluoride with trifluoroethylene in the liquid phase according to the invention may be carried out in the absence of catalyst.

In the process according to the invention, the reaction of hydrogen fluoride with trifluoroethylene in the liquid phase is advantageously carried out in the presence of a catalyst. The catalyst may comprise any compound conventionally mentioned for catalysing the hydrofluorination of olefins.

In a preferred embodiment of the process according to the invention, the catalyst comprises a halide and/or an oxide of a metal chosen from titanium and tin.

Halide and/or oxide of a metal chosen from titanium and tin is understood to denote a halide or an oxide of titanium, a halide or an oxide of tin, a mixture of these halides and/or of these oxides, a mixed halide of titanium and of tin, a mixed oxide of titanium and of tin or an oxyhalide of titanium and/or of tin.

Halide is understood to denote one or a number of salts formed from one or a number of halogens.

The catalyst preferably comprises at least 50% by weight of halide and/or oxide of a metal chosen from titanium and tin. More preferentially still, the catalyst consists essentially of halide and/or oxide of a metal chosen from titanium and tin.

The catalyst used in this preferred embodiment of the invention is simple to prepare, is inexpensive and presents a very advantageous degree of conversion of trifluoroethylene and a very advantageous selectivity towards 1,1,1,2-tetrafluoroethane.

In the abovesaid preferred embodiment of the invention, a chloride or a fluoride is advantageously adopted as halide of a metal chosen from titanium and tin. The use of a chloride is advantageous in that this compound is inexpensive and readily available. In particular, a tetrachloride is chosen. The use of a fluoride has also given good results. In particular, a tetrafluoride is chosen.

In a particularly preferred way, a chlorofluoride is chosen as halide. This variant of the invention would have the advantageous characteristic of first limiting the formation of hydrogen chloride by incidental reaction of the catalyst with the hydrogen fluoride used for treating trifluoroethylene and, then, the subsequent reaction of the hydrogen chloride thus formed with trifluoroethylene to form undesirable 1-chloro-1,1,2-trifluorethane (HFA-133b). This explanation, however, does not bind the Applicant. More preferentially still, a compound of formula $TiCl_{4-x}F_x$ or $SnCl_{4-x}F_x$, x being between 0 and 4, is used. Excellent results have been obtained when x is at least equal to 1.

There is advantageously used a catalyst obtained from a halide other than a fluoride which is subjected beforehand to an at least partial fluorination. This fluorination may, in particular, be carried out by means of hydrogen fluoride.

Advantageously, a dioxide of titanium or of tin is adopted as the oxide of titanium or of tin.

In the case of an oxyhalide, the latter may be obtained, for example, by a prior halogenation of an oxide. In particular, an oxide may be subjected beforehand to an at least partial fluorination. This fluorination may more particularly be carried out by means of hydrogen fluoride.

Titanium is preferred as the metal, especially in view of its lesser effects on the environment.

In the process according to the invention, the catalyst may be used in variable amounts. It is generally used at a concentration of at least approximately 0.001 mol of catalyst per mole of trifluoroethylene. Very good results have been obtained in the presence of at least approximately 0.005 mol of catalyst per mole of trifluoroethylene. In principle, there is no upper limit to the amount of catalyst used. In practice however, most often there is not used more than approximately 5 mol of catalyst per mole of trifluoroethylene. Preferably, there is not exceeded approximately 0.5 mol, and more preferentially still there is not exceeded approximately 0.1 mol, of catalyst per mole of trifluoroethylene.

In the process according to the invention, hydrogen fluoride and trifluoroethylene may be used in variable molar ratios. Generally, at least approximately 0.1 mol of hydrogen fluoride per mole of trifluoroethylene is used. Preferably, this ratio is at least approximately 1. Most often, there is not exceeded approximately 20 mol of hydrogen fluoride per mole of trifluoroethylene, the values not exceeding approximately 10 being especially recommended.

The process according to the invention may be carried out in a wide temperature range. Generally, this temperature is at least approximately 30° C. Preferably, it is at least approximately 50° C. A temperature of at least approximately 70° C. makes a faster reaction possible. Most often, especially depending on the acceptable pressure, this temperature does not exceed approximately 150° C., temperatures lower than or equal to approximately 110° C. being especially recommended.

The pressure is not critical in itself, as long as it makes it possible for the process according to the invention to be used in the liquid phase. This pressure may be the autogenous pressure, a higher pressure generated by the introduction of an inert gas, such as for example nitrogen, or a low pressure obtained by dilution of the reaction mixture with an inert organic solvent, such as for example 1,2-dichloroethane.

The process according to the invention may be implemented continuously or noncontinuously. The residence time of the reactants in the reactor is generally at least approximately 5 minutes. Preferably, it is at least approximately 15 minutes. Most often, this residence time does not exceed approximately 5 hours, the values lower than or equal to approximately 2 hours being especially recommended. When the process according to the invention is implemented in the absence of catalyst, the residence times are preferably longer than those adopted under analogous conditions in the presence of catalyst.

The process according to the invention may be implemented in any type of reactor or equipment making it possible to combine the conditions described and, in particular, to withstand pressure and hydrogen fluoride. Reactors made of steel, of stainless steel or of alloys, such as those known under the tradenames Monel, Inconel or Hastelloy, are often used. Reactors coated with an inert metal or alloy, or covered with a resin which is inert under the conditions of the process, for example a fluorinated resin, may also be used.

The examples below illustrate the invention in a non-limiting way.

EXAMPLE 1

A vacuum of $4 \times 10^3$ Pa was produced in a 250 cm³ reactor which is equipped with a magnetic stirrer, a temperature sensor and a manometer and which is covered on the inside with PVDF.

31 g (1.55 mol) of HF arising from a cylinder pressurised at $4 \times 10^5$ Pa by nitrogen were then introduced therein at room temperature. The reactor was then charged with 58.7 g (0.716 mol) of trifluoroethylene, also at room temperature.

The reactor was placed in a preheated oil bath in order to bring it to and to maintain it at an internal temperature of approximately 90° C.

Samples were withdrawn in the liquid phase, discharged through a scrubber containing water at 40° C. and their content of organic compounds analysed by gas phase chromatography.

Table 1 illustrates the operating conditions and the results obtained.

TABLE 1

|  | t = 0 (*) | t = 160 min | t = 220 min |
|---|---|---|---|
| Internal temperature [°C.] | — | 89.9 | 89.4 |
| Oil bath temperature [°C.] | — | 129 | 131 |
| Pressure [$10^5$ Pa] | — | 18.5 | 13.1 |
| Composition [%] |  |  |  |
| Trifluoroethylene | — | 54.7 | 41.5 |
| 1,1,1,2-tetra-fluoroethane | — | 45.3 | 58.5 |

(*) 10 minutes before having reached the desired temperature in the reactor, i.e. 60 minutes after introduction of the reactor into the oil bath (in order to take into account the conversion during the temperature rise).

EXAMPLE 2

5.9 g (0.030 mol) of $SnF_4$ were introduced, at room temperature and ambient pressure, into a 250 cm³ reactor equipped with a magnetic stirrer, a temperature sensor and a manometer.

A vacuum of $4 \times 10^3$ Pa was produced in the reactor. 24.7 g (1.23 mol) of HF arising from a cylinder pressurised at $4 \times 10^5$ Pa by nitrogen were then introduced therein at room temperature. The reactor was then charged with 62.7 g (0.764 mol) of trifluoroethylene, also at room temperature.

The reactor was placed in a preheated oil bath in order to bring it to and to maintain it at an internal temperature of approximately 90° C.

Samples were withdrawn in the gas phase, discharged through a scrubber containing water at 40° C. and their content of organic compounds analysed by gas phase chromatography.

Table 2 illustrates the operating conditions and the results obtained.

TABLE 2

|  | t = 0 (*) | t = 25 min | t = 55 min |
|---|---|---|---|
| Internal temperature [°C.] | — | 86.8 | 91.4 |
| Oil bath temperature [°C.] | — | 143 | 143 |
| Pressure [$10^5$ Pa] | — | 25 | 25 |
| Composition [%] |  |  |  |
| Trifluoroethylene | — | 3.0 | 1.5 |
| 1,1,1,2-tetra-fluoroethane | — | 96.9 | 98.4 |

(*) 10 minutes before having reached the desired temperature in the reactor, i.e. 5 minutes after introduction of the reactor into the oil bath (in order to take into account the conversion during the temperature rise).

EXAMPLE 3 a) Preparation of the Catalyst 8 g (0.031 mol) of $SnCl_4$ were introduced at room temperature and ambient pressure into a 250 cm³ reactor equipped with a magnetic stirrer, a temperature sensor and a manometer.

A vacuum of $4 \times 10^3$ Pa was produced in the autoclave and 34.2 g (1.71 mol) of HF arising from a cylinder pressurised at $4 \times 10^5$ Pa by nitrogen were introduced therein at room temperature.

The reactor was then heated in an oil bath until it had reached an internal temperature of 90° C., which was maintained for 6 hours.

The reactor was then cooled to room temperature and part of the excess HF, and the HCl formed, were removed through a scrubber containing 400 cm$^3$ of water at 25° C. until atmospheric pressure was reached.

The Cl$^-$ content of the scrubber was then 1.39 g, which corresponds to a Cl$^-$/F$^-$ exchange of 31.6% and thus to a catalytic composition of formula SnCl$_{2.7}$F$_{1.3}$.

b) Hydrofluorination of Trifluoroethylene

The reactor containing the catalyst prepared above was maintained at room temperature and placed under a vacuum of 4×10$^3$ Pa, which made it possible to remove virtually all the excess HF used during the preparation of the catalyst. It was then supplied with 37.1 g (1.85 mol) of HF at room temperature, arising from a cylinder pressurised at 4×10$^5$ Pa by nitrogen. The reactor was then charged with 44.9 g (0.547 mol) of trifluoroethylene, also at room temperature.

The reactor was placed in a preheated oil bath in order to bring it to and to maintain it at an internal temperature of approximately 90° C.

Samples were withdrawn in the gas phase, discharged through the scrubber containing water at 40° C. and their content of organic compounds analysed by gas phase chromatography.

Table 3 illustrates the operating conditions and the results obtained.

TABLE 3

|  | t = 0 (*) | t = 55 min |
|---|---|---|
| Internal temperature [°C.] | 76.5 | 94.5 |
| Oil bath temperature [°C.] | 119 | 144 |
| Pressure [°C.] | 20.5 | 27 |
| Composition [%] |  |  |
| Trifluoroethylene | — | 0.35 |
| 1,1,1,2-tetra-fluoroethane | — | 99.5 |

(*) 10 minutes before having reached the desired temperature in the reactor, i.e. 30 minutes after introduction of the reactor into the oil bath (in order to take into account the conversion during the temperature rise).

Examples 2 and 3 illustrate the excellent degree of conversion of the trifluoroethylene and the very high selectivity towards 1,1,1,2-tetrafluoroethane obtained by means of the process according to the invention, in the presence of a tin-based catalyst.

EXAMPLE 4 a) Preparation of the Catalyst 6.1 g (0.0322 mol) of TiCl$_4$ were introduced at room temperature and ambient pressure into a 250 cm$^3$ reactor equipped with a magnetic stirrer, a temperature sensor and a manometer.

A vacuum of 4×10$^3$ Pa was produced in the reactor and 31.1 g (1.55 mol) of HF, arising from a cylinder pressurised at 4×10$^5$ Pa by nitrogen, were introduced therein.

After 30 minutes at room temperature, part of the HF excess, and the HCl formed, were removed through a scrubber containing 400 cm$^3$ of water at 25° C. until atmospheric pressure was reached.

The Cl$^-$ content of the scrubber was then 4.41 g, which corresponds to a Cl$^-$/F$^-$ exchange of 96.6% and thus to a catalytic composition of formula TiCl$_{0.1}$F$_{3.9}$.

b) Hydrofluorination of Trifluoroethylene

The reactor containing the catalyst prepared above was maintained at room temperature and placed under a vacuum of 4×10$^3$ Pa, which made it possible to remove virtually all the excess HF used during the preparation of the catalyst. It was then supplied with 28.7 g (1.43 mol) of HF at room temperature, arising from a cylinder pressurised at 4×10$^5$ Pa by nitrogen. The reactor was then charged with 52.4 g (0.639 mol) of trifluoroethylene, also at room temperature.

The reactor was placed in a preheated oil bath in order to bring it to and to maintain it at an internal temperature of approximately 90° C.

Samples were withdrawn in the liquid phase, discharged through the scrubber containing water at 40° C. and their content of organic compounds analysed by gas phase chromatography.

Table 4 illustrates the operating conditions and the results obtained.

TABLE 4

|  | t = 0 (*) | t = 10 min | t = 40 min |
|---|---|---|---|
| Internal temperature [°C.] | — | 90.8 | 86.9 |
| Oil bath temperature [°C.] | — | 110 | 121 |
| Pressure [10$^5$ Pa] | — | 26.5 | 22.8 |
| Composition [%] |  |  |  |
| Trifluoroethylene | — | 10.9 | 0.4 |
| 1,1,1,2-tetra-fluoroethane | — | 88.9 | 99.5 |

(*) 10 minutes before having reached the desired temperature in the reactor, i.e. 5 minutes after introduction of the reactor into the oil bath (in order to take into account the conversion during the temperature rise).

Example 4 illustrates the easier preparation of a titanium-based catalyst and the greater speed of the process according to the invention in the presence of this catalyst.

EXAMPLE 5 a) Preparation of the Catalyst 6.1 g (0.032 mol) of TiCl$_4$ were introduced at room temperature and ambient pressure into a 250 cm$^3$ reactor equipped with a magnetic stirrer, a temperature sensor and a manometer.

A vacuum of 4×10$^3$ Pa was produced in the reactor and 26.2 g (1.31 mol) of HF, arising from a cylinder pressurised at 4×10$^5$ Pa by nitrogen, were introduced therein at room temperature.

After 30 minutes at room temperature, part of the excess HF, and the HCl formed, were removed through a scrubber containing 400 cm$^3$ of water at 25° C. until atmospheric pressure was reached.

The Cl$^-$ content of the scrubber was then 4.35 g, which corresponds to a Cl$^-$/F$^-$ exchange of 95.3% and thus to a catalytic composition of formula TiCl$_{0.2}$F$_{3.8}$.

b) Hydrofluorination of Trifluoroethylene

The reactor containing the catalyst prepared above was maintained at room temperature and placed under a vacuum of 4×10$^3$ Pa, which made it possible to remove virtually all the excess HF used during the preparation of the catalyst. It was then supplied with 33.4 g (1.67 mol) of HF at room temperature, arising from a cylinder pressurised at 4×10$^5$ Pa by nitrogen. The reactor was then charged with 50 g (0.61 mol) of trifluoroethylene, also at room temperature.

The reactor was placed in a preheated oil bath in order to bring it to and to maintain it at an internal temperature of approximately 50° C.

Samples were withdrawn in the liquid phase, discharged through the scrubber containing water at 40° C. and their content of organic compounds analysed by gas phase chromatography.

Table 5 illustrates the operating conditions and the results obtained.

TABLE 5

|  | t = 0 (*) | t = 40 min | t = 70 min |
|---|---|---|---|
| Internal temperature [°C.] | — | 47.6 | 50.4 |
| Oil bath temperature [°C.] | — | 57 | 61 |
| Pressure [$10^5$ Pa] | — | 10.5 | 10 |
| Composition [%] |  |  |  |
| Trifluoroethylene | — | 6.3 | 1.8 |
| 1,1,1,2-tetra-fluoroethane | — | 93.6 | 98.1 |

(*) 10 minutes before having reached the desired temperature in the reactor, i.e. 5 minutes after introduction of the reactor into the oil bath (in order to take into account the conversion during the temperature rise).

Example 5 illustrates the feasibility of the process according to the invention at a lower temperature, but with a slower conversion.

We claim:

1. A process for the preparation of 1,1,1,2,-tetrafluoroethane consisting essentially of reacting hydrogen fluoride with trifluoroethylene, the reaction being carried out in the liquid phase in the presence of a catalyst consisting essentially of titanium or tin halide, oxide or oxyhalide.

2. The process according to claim 1, wherein chloride or fluoride is chosen as halide.

3. The process according to claim 2, wherein tetrachloride or tetrafluoride is chosen as chloride or fluoride.

4. The process according to claim 1, wherein the chlorofluoride is chosen as halide.

5. The process according to claim 1, wherein the catalyst is obtained starting from a halide other than a fluoride which is subjected beforehand to an at least partial fluorination.

6. The process according to claim 5, wherein the prior fluorination is carried out by means of hydrogen fluoride.

7. The process according to claim 1, wherein a dioxide is chosen as oxide.

8. The process according to claim 1, wherein the metal chosen is titanium.

9. The process according to claim 1, wherein the catalyst is used at a concentration from approximately 0.001 to approximately 5 mol of catalyst per mole of trifluororethylene.

10. The process according to claim 1, wherein the hydrogen fluoride is used at a concentration from approximately 0.1 to approximately 20 mol of hydrogen fluoride per mole of trifluoroethylene.

11. A process for the preparation of 1,1,1,2-tetrafluoroethane by reaction of hydrogen fluoride with trifluoroethylene, consisting essentially of reacting being carried out in the liquid phase in the presence of a catalyst consisting essentially of a compound of the formula $TiCl_{4-x}F_x$ or $SnCl_{4-x}F_x$, x being between 0 and 4.

* * * * *